US008888763B2

(12) United States Patent
Ramstein et al.

(10) Patent No.: US 8,888,763 B2
(45) Date of Patent: Nov. 18, 2014

(54) TOOL HAVING MULTIPLE FEEDBACK DEVICES

(71) Applicant: Immersion Corporation, San Jose, CA (US)

(72) Inventors: Christophe Ramstein, San Fransico, CA (US); Christopher J. Ullrich, Ventura, CA (US); Danny A. Grant, Laval (CA)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 13/900,816

(22) Filed: May 23, 2013

(65) Prior Publication Data

US 2013/0253483 A1 Sep. 26, 2013

Related U.S. Application Data

(63) Continuation of application No. 12/327,104, filed on Dec. 3, 2008, now abandoned.

(51) Int. Cl.
*A61B 17/00* (2006.01)
*A61B 17/29* (2006.01)
*A61B 19/00* (2006.01)

(52) U.S. Cl.
CPC ........... *A61B 17/00234* (2013.01); *A61B 17/29* (2013.01); *A61B 2017/00022* (2013.01); *A61B 2017/00115* (2013.01); *A61B 2017/00199* (2013.01); *A61B 2019/2292* (2013.01); *A61B 2019/465* (2013.01); *A61B 2019/4857* (2013.01); *A61B 2019/5229* (2013.01)
USPC ............................... 606/1; 715/702; 715/771

(58) Field of Classification Search
USPC ............................................................ 606/1
See application file for complete search history.

(56) References Cited

U.S. PATENT DOCUMENTS 5,503,320 A * 4/1996 Webster et al. ............. 227/176.1
5,607,436 A * 3/1997 Pratt et al. .................... 606/143
5,827,178 A * 10/1998 Berall ........................... 600/185
5,928,137 A * 7/1999 Green ........................... 600/160

(Continued)

FOREIGN PATENT DOCUMENTS

CA 2 520 942 A1 3/2007
EP 1769756 A1 4/2007

(Continued)

OTHER PUBLICATIONS

International Search Report and Written Opinion, PCT/US2009/065034, (Feb. 4, 2010).

(Continued)

*Primary Examiner* — William Thomson
*Assistant Examiner* — John R Downey
(74) *Attorney, Agent, or Firm* — Medler Ferro PLLC (57) ABSTRACT

Disclosed herein are systems and methods for managing how signals, which are sensed on a tool, are presented to an operator of the tool. According to one example of a method for managing signals, the method comprises allowing an operator to manipulate a tool having a plurality of output mechanisms mounted thereon. The method also includes sensing a property of an object located near or adjacent to a distal portion of the tool and processing the sensed property to obtain one or more output signals. Furthermore, the method includes applying the one or more output signals to one or more of the output mechanisms.

7 Claims, 4 Drawing Sheets

(56) References Cited

U.S. PATENT DOCUMENTS

| | | | |
|---|---|---|---|
| 6,053,906 A * | 4/2000 | Honda et al. ............... 606/1 |
| 6,139,489 A | 10/2000 | Wampler et al. |
| 6,223,100 B1 * | 4/2001 | Green ............... 700/264 |
| 6,424,885 B1 * | 7/2002 | Niemeyer et al. ............... 700/245 |
| 6,429,846 B2 | 8/2002 | Rosenberg et al. |
| 6,536,536 B1 * | 3/2003 | Gass et al. ............... 173/2 |
| 6,641,595 B1 | 11/2003 | Moran et al. |
| 6,671,581 B2 * | 12/2003 | Niemeyer et al. ............... 700/245 |
| 6,810,281 B2 * | 10/2004 | Brock et al. ............... 600/427 |
| 6,822,635 B2 | 11/2004 | Shahoian et al. |
| 7,148,875 B2 * | 12/2006 | Rosenberg et al. ............... 345/156 |
| 7,155,315 B2 * | 12/2006 | Niemeyer et al. ............... 700/245 |
| 7,245,292 B1 | 7/2007 | Custy |
| 7,382,357 B2 | 6/2008 | Panotopoulos et al. |
| 7,450,110 B2 * | 11/2008 | Shahoian et al. ............... 345/173 |
| 7,479,903 B2 * | 1/2009 | Otsuka et al. ............... 341/22 |
| 7,540,872 B2 * | 6/2009 | Schechter et al. ............... 606/50 |
| 7,548,232 B2 * | 6/2009 | Shahoian et al. ............... 345/173 |
| 7,728,820 B2 * | 6/2010 | Rosenberg et al. ............... 345/173 |
| 8,016,818 B2 | 9/2011 | Ellis et al. |
| 8,120,301 B2 * | 2/2012 | Goldberg et al. ............... 318/581 |
| 8,140,141 B2 * | 3/2012 | McGreevy et al. ............... 600/317 |
| 2001/0025150 A1 | 9/2001 | De Juan et al. |
| 2001/0039419 A1 * | 11/2001 | Francischelli et al. ............... 606/42 |
| 2002/0120188 A1 | 8/2002 | Brock et al. |
| 2002/0143275 A1 | 10/2002 | Sarvazyan et al. |
| 2002/0177848 A1 * | 11/2002 | Truckai et al. ............... 606/50 |
| 2003/0057973 A1 * | 3/2003 | Nojima et al. ............... 324/753 |
| 2003/0179190 A1 | 9/2003 | Franzen |
| 2005/0131390 A1 * | 6/2005 | Heinrich et al. ............... 606/1 |
| 2006/0119586 A1 | 6/2006 | Grant et al. |
| 2007/0135735 A1 * | 6/2007 | Ellis et al. ............... 600/587 |
| 2007/0142825 A1 * | 6/2007 | Prisco et al. ............... 606/1 |
| 2007/0182718 A1 | 8/2007 | Schoener et al. |
| 2007/0229233 A1 | 10/2007 | Dort |
| 2007/0236450 A1 | 10/2007 | Colgate et al. |
| 2008/0132313 A1 | 6/2008 | Rasmussen et al. |
| 2008/0252607 A1 | 10/2008 | De Jong et al. |
| 2008/0297475 A1 | 12/2008 | Woolf et al. |
| 2008/0300580 A1 * | 12/2008 | Shelton et al. ............... 606/1 |
| 2008/0303795 A1 | 12/2008 | Lowles et al. |
| 2009/0002328 A1 | 1/2009 | Ullrich et al. |
| 2009/0128503 A1 | 5/2009 | Grant et al. |
| 2009/0167704 A1 * | 7/2009 | Terlizzi et al. ............... 345/173 |
| 2009/0209979 A1 * | 8/2009 | Yates et al. ............... 606/143 |
| 2009/0234273 A1 * | 9/2009 | Intoccia et al. ............... 604/22 |
| 2010/0179423 A1 * | 7/2010 | Ramstein et al. ............... 600/437 |
| 2010/0193566 A1 * | 8/2010 | Scheib et al. ............... 227/175.2 |
| 2011/0004199 A1 * | 1/2011 | Ross et al. ............... 606/1 |
| 2011/0046659 A1 * | 2/2011 | Ramstein et al. ............... 606/205 |
| 2012/0010506 A1 * | 1/2012 | Ullrich ............... 600/440 |

FOREIGN PATENT DOCUMENTS

| | | |
|---|---|---|
| WO | WO-97/41767 | 11/1997 |
| WO | WO-01/49227 A1 | 7/2001 |
| WO | WO-03/020139 A2 | 3/2003 |

OTHER PUBLICATIONS

Laparoscopic Tool Redesign, University of Nebraska Medical Center, Center for Advanced Surgical Technology (CAST), http://www.unmc.edu/dept/mis/index.cfm?CONREF=4, printed Jul. 1, 2008, 1 page.

Dargahi, J., An endoscopic force-position sensor grasper with minimum sensors, Canadian Journal of Electrical and Computer Engineering, vol. 28, Issue 3, Jul.-Oct. 2003, Summary, http://ieeexplore.ieee.org/Xplore/login.jsp?url=ie15/9754/30768/01425102.pdf?arnumber=1, printed on Jul. 1, 2008, 1 page.

ENDO CLIP™ III Clip Applier With Clip Logic Technology, autosuture advancing possibilities in surgery, www.autosuture.com/AutoSuture/pagebuilder.aspx?topicID=157721, printed on Sep. 12, 2008, 3 pages.

Dargahi, J., An integrated force-position tactile sensor improving diagnostic and therapeutic endoscopic surgery, Bio-Medical Materials and Engineering, IOS Press, vol. 14, No. Feb. 2004, Abstract, http://iospress.metapress.com/content/0k8v0960v9vpr6nw/, printed on Jul. 1, 2008, 2 pages.

Maria Vatshaug Ottermo, Virtual Palpation Gripper, A Dissertation Submitted in Partial Fulfillment of the Requirements for the Degree of Philosophiae Doctor, PhD, Department of Engineering Cybernetics, Norwegian University of Science and Technology, 2006, pp. 1-139.

\* cited by examiner

FIG. 8

TOOL HAVING MULTIPLE FEEDBACK DEVICES

CROSS-REFERENCE TO RELATED APPLICATION

The present application is a continuation of U.S. application Ser. No. 12/327,104 filed on Dec. 3, 2008, which is incorporated by reference herein in its entirety.

TECHNICAL FIELD

The embodiments of the present disclosure generally relate to hand tools and more particularly relate to sensing a property of an object in the vicinity of a hand tool and displaying the property in one or more output modes.

BACKGROUND

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

During minimally invasive surgery, the surgeon can introduce a miniature camera through an incision. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, etc. Compared to open surgery, however, minimally invasive surgery can present limitations regarding the surgeon's ability to see and feel the patient's organs and tissues.

SUMMARY

The present disclosure describes a number of embodiments of systems and methods for managing how sensed signals are provided to an operator of a tool, which includes a sensor for sensing the signals. In one embodiment, for example, a method for managing signals includes allowing an operator to manipulate a tool having a plurality of output mechanisms mounted thereon. The method also includes sensing a property of an object located near or adjacent to a distal portion of the tool and processing the sensed property to obtain one or more output signals. The method also includes applying the one or more output signals to one or more of the output mechanisms.

The embodiments described in the present disclosure may include additional features and advantages, which may not necessarily be expressly disclosed herein but will be apparent to one of ordinary skill in the art upon examination of the following detailed description and accompanying drawings. It is intended that these additional features and advantages be included and encompassed within the present disclosure.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Although minimally invasive surgical procedures involving small incisions include many advantages over open surgery, minimally invasive surgery can still create challenges to a surgeon. For example, the surgeon must typically rely on a camera to view the patient's internal organs and see how the movement and operation of the tools affects the organs. To enhance the surgeon's experience, feedback can be provided to the surgeon to communicate information about how the body of the patient reacts to the tools. According to the teaching of the present disclosure, output can be provided to the surgeon in multiple ways, e.g., visually, audibly, tactilely, etc. Information regarding the status of feedback devices can also be provided to the surgeon as well.

The present disclosure describes embodiments that include any type of tools that can be manipulated by an operator. More particularly, the tools described in the present disclosure include a handle portion that mechanically controls a distal portion of the tool. Mounted on the distal portion are one or more sensors configured to sense a parameter of an object that interacts with the tool. The sensed signals can be processed to obtain stimulation signals designed to be provided to one or more output mechanisms, such as, for example, haptic actuation devices, vibrotactile feedback devices, kinesthetic feedback devices, visual displays, speakers or other audio devices, etc.

Although many of the examples described in the embodiments of the present disclosure relate to surgical tools, such as minimally invasive surgical tools, it should be understood that the present disclosure also encompasses other types of tools as well. In addition, although many of examples herein relate to surgical patients and how the organs and tissues of the patient interact with the surgical tools, it should also be understood that the present disclosure may also refer to other objects that are intended to interact with or react to the operations of the respective tools. Other features and advantages will be apparent to one of ordinary skill in the art upon reading and understanding the general principles of the present disclosure and are intended to be included herein.

Figure 1:
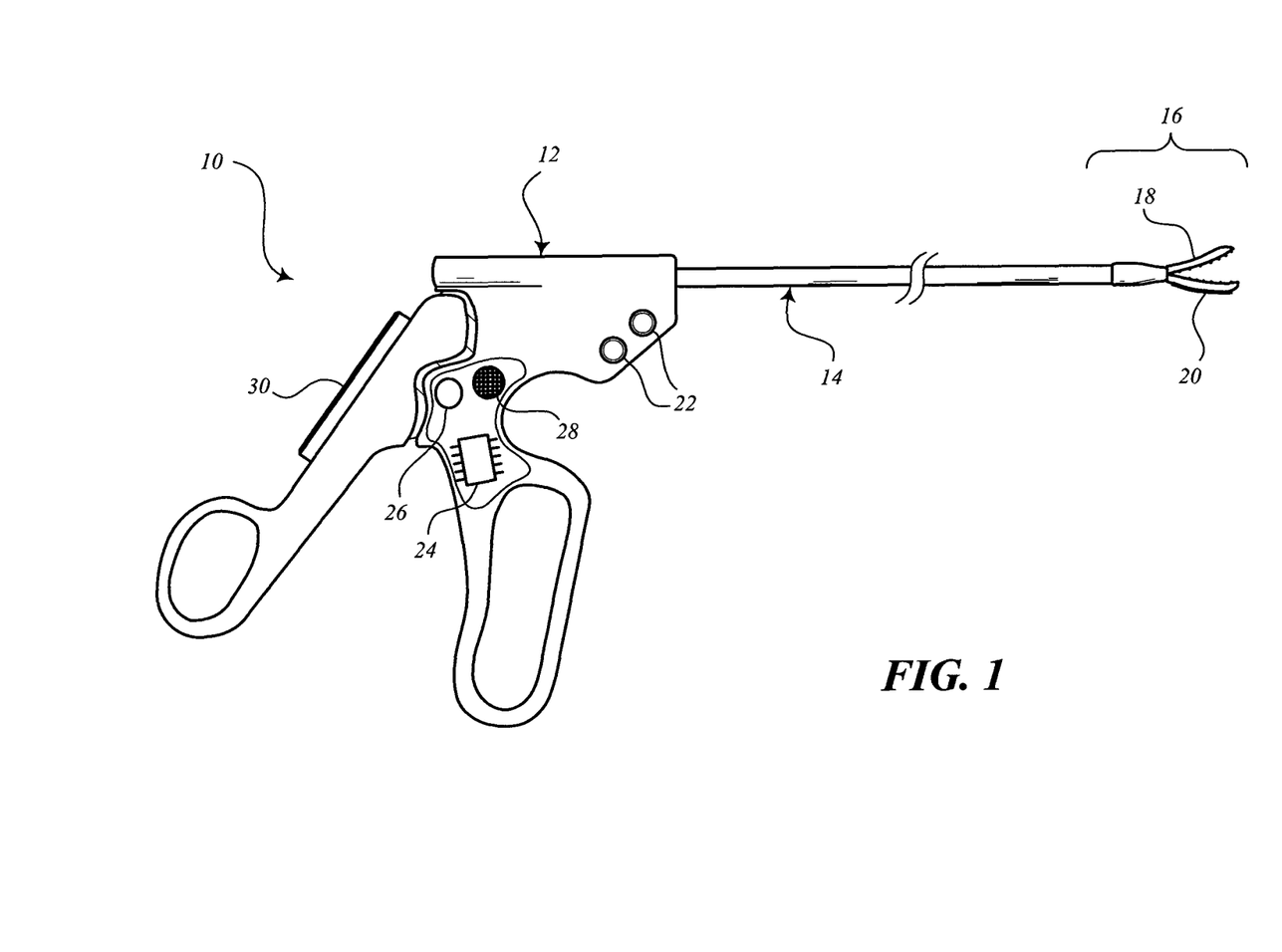
FIG. 1 is a diagram illustrating a side view of a surgical tool according to one embodiment.

FIG. 1 is a diagram illustrating an embodiment of a surgical tool 10. In this diagram, surgical tool 10 is shown as a laparoscopic tool, which is configured to be inserted through a small incision in the abdomen of a patient. Surgical tool 10 in this embodiment includes a handle 12, a shaft 14, and a distal portion 16. Shaft 14 is designed to connect handle 12 to distal portion 16 and to communicate mechanical actions of handle 12 to distal portion 16. Shaft 14 is further designed to communicate electrical signals from distal portion 16 back to handle 12 as explained in more detail below.

According to the embodiment of FIG. 1, distal portion 16 includes a tip 18 and a sensing device 20 formed on tip 18. As shown, tip 18 is a grasper. However, it should be understood that distal portion 16 may include any suitable type of tip having any suitable functionality. Also, in other alternative embodiments, sensing device 20 may be connected to any part of distal portion 16 or even other parts of tip 18. According to some examples of the embodiment of FIG. 1, shaft 14 may be about 20 cm to 30 cm in length and tip 18 may be about 10 mm to 15 mm in length.

According to the embodiment of FIG. 1, handle portion 12 of surgical tool 10 further includes one or more buttons 22. Buttons 22 can be configured using any suitable mechanism for allowing an operator to control the nature of the feedback that is provided to the operator. Buttons 22 may include devices for allowing certain levels to be adjusted or certain selections to be made regarding the output presented to the operator. In some embodiments, buttons 22 may be configured as switches, such as momentary toggle switches, allowing an operator to select different ways in which sensor information is mapped or provided to respective output devices. Buttons 22 can be implemented as a rocker switch or as a one-dimensional control surface.

Handle portion 12 also includes a processing device 24, haptic actuator 26, and a speaker 28, which are shown through a cut out in handle portion 12. Processing device 24, haptic actuator 26, and speaker 28 can be mounted on a printed circuit board (not shown), which includes circuitry for electrically coupling the components. The circuitry on the printed circuit board may include any suitable amplification and attenuation type circuitry, power sources for providing and regulating power to each component, and other circuitry for proper operation of processing device 24 and other components as would be understood by one of ordinary skill in the art. In some embodiments, haptic actuator 26 can be implemented as an inertial actuator to provide vibrotactile feedback to the operator. Haptic actuator 26 may include an eccentric rotating mass ("ERM") actuator, linear resonant actuator ("LRA"), piezoelectric actuator, shape memory alloy, electro-active polymer, or other suitable type of actuating device.

In this embodiment of FIG. 1, handle portion 12 also supports a level meter 30. As illustrated, level meter 30 is mounted on a back section of handle portion 12, which is designed for normal conformity with the operator's thumb. Level meter 30 may be a visual feedback device to show certain levels that can be adjusted by the operator. For example, by using buttons 22, the operator can generally adjust how signals sensed by sensing device 20 are processed and presented to the operator. According to one function of buttons 22, the operator can enable or disable one or more output mechanisms by controlling whether or not output signals based on the sensed signals are provided to the respective output devices. Another function of buttons 22 includes the ability to enable one or more output mechanisms. According to FIG. 1, the output mechanisms can include at least haptic actuator 26, speaker 28, and level meter 30. In this regard, the operator can control if and how sensed signals are presented in a visual, auditory, and/or haptic fashion.

The different output mechanisms may be used to cooperatively communicate a single property. In some embodiments, however, they can represent distinct components of the processed sensor signals or other parameters. In some cases, one or more of the output mechanisms may be configured to provide both sensor signal information and adjustment level information, depending on the particular application.

Furthermore, buttons 22 can be used to adjust the level, intensity, or amplitude at which the output mechanisms provide the respective output. For example, the operator may wish to disable haptic actuator 26, but enable speaker 28 and have its volume turned down low.

By manipulating handle 12, an operator can insert distal portion 16 into the abdomen of the patient and control tip 18 of distal portion 16. When distal portion 16 is inserted, the surgeon can further manipulate handle 12 to control the location and orientation of tip 18 such that sensing device 20 is able to contact certain regions of the patient. Sensing device 20 may include one or more sensors each configured to measure or test any desired parameter of the patient, such as pulse, for example. In some embodiments in which sensing device 20 does not necessarily need to contact a particular region of the patient, tip 18 can be controlled to position sensing device 20 to accomplish certain contactless sensing functions.

Sensing device 20 can be configured to sense any suitable property of the object under test. For instance, sensing device 20 can be configured as pressure sensors using resistive or capacitive pressure sensing technologies. Alternatively, sensing device 20 can include strain gauges, piezoelectric sensors, stiffness sensors, etc. As strain gauges, sensing device 20 can provide additional information about contact force to finely tune a generally coarse measurement of force. As piezoelectric sensors, sensing devices 20 can generate ultrasound signals that reflect off portions of the object. In this case, echo signals can be detected by sensing device 20 to determine the location of objects. Sensing device 20 can also be configured as stiffness sensors that can detect nodules, e.g., tumors, or other stiff regions.

The features illustrated and described with respect to FIG. 1 may also be incorporated within the embodiments shown with respect to FIGS. 2-6 as described below. However, for the sake of brevity, many features shown in some drawings may not be shown in other drawings. Also, the description of similar elements in different drawings is not repeated. It should be appreciated, however, that although one or more embodiments may not include features described with respect to other embodiments, some or all of the features may still be included therein as would be recognized from an understanding of the present disclosure.

Figure 2:
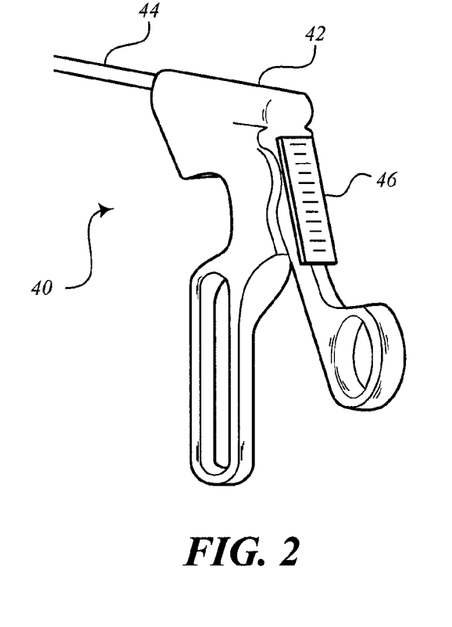
FIG. 2 is a diagram illustrating a rear perspective view of a surgical tool having a level meter mounted thereon, according to one embodiment.

FIG. 2 is a diagram showing an embodiment of a surgical tool 40 from a rear perspective. In this diagram, only a handle portion 42 and a part of a shaft 44 are shown of surgical tool 40, which may further include other features, such as a sensing device at a distal end. On a back region of handle portion 42, surgical tool 40 in this embodiment includes a level meter 46. Level meter 46 may include the same functionality as level meter 30 shown in FIG. 1. Level meter 46 can be configured to display any type of visual information to the operator. In particular, level meter 46 may be designed, for example, to display values, levels, and/or percentages of properties of the object being sensed by a distal sensor.

Level meter 46 may be an interactive control surface allowing the user to adjust the properties of the output mechanisms. Level meter 46 can receive touch information from the user to make adjustments. Also, level meter 46 can display status information of one or more output mechanisms mounted on surgical tool 40. In this regard, the status information can include whether a respective output mechanism is enable or disabled, the level of intensity, strength, or magnitude of the signal supplied to the respective output mechanism, or other parameters of the respective output mechanisms. Regarding parameters with respect to visual display devices, for example, certain picture quality parameters can be adjusted. Regarding parameters with respect to audio devices, for example, frequency, fade time, and other auditory parameters can be adjusted. Regarding parameters with respect to haptic actuating devices, for example, frequency, intensity, and other various haptic parameters can be adjusted.

Figure 3:
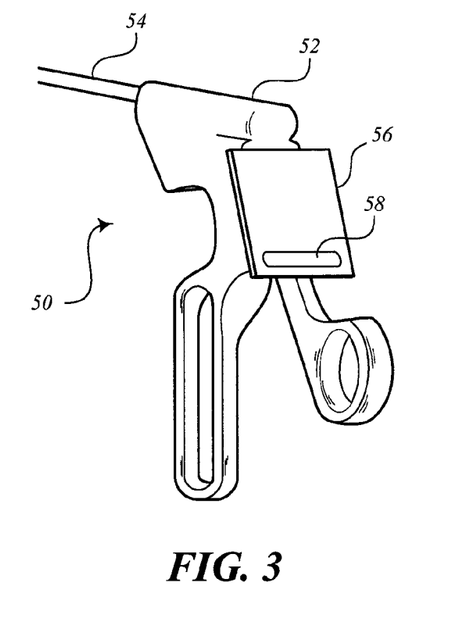
FIG. 3 is a diagram illustrating a rear perspective view of a surgical tool having an LCD screen mounted thereon, according to one embodiment.

FIG. 3 is a diagram showing an embodiment of a surgical tool 50 from a rear perspective view. In this diagram, only a handle portion 52 and a part of a shaft 54 are shown of surgical tool 50, which may include other features, such as a sensing device at a distal end thereof. On a back region of handle portion 52, surgical tool in this embodiment includes a liquid crystal display (LCD) screen 56. LCD screen 56 may be used to display visual information regarding the object sensed at a distal end of surgical tool 50. In some embodiments, the sensor at the distal end may contain a camera or other type of image capture device. In this case, images can be presented on LCD screen 56 to assist the surgeon to position the tool as needed. LCD screen 56 may also be configured to show ultrasound, x-ray, or other types of radiation-based image information.

LCD screen 56 can include a touchscreen, which can be configured to present information, e.g., visual information, to the operator. Also, the touchscreen can also be configured to sense when the operator presses certain portions of the touchscreen. In this way, the touchscreen can act as a touchable user interface with graphical presentation capabilities. In some embodiments, LCD screen 56 may be designed with a surface that changes shape or size based on signals being sensed. For example, the surface of LCD screen 56 may be able to adjust its topography to provide an indication of the topography or other feature of the object being sensed.

LCD screen 56 can include supplemental information, which may depend on the context of the particular surgical procedure being performed. Information may include, for example, pre-operative information, intra-operative information, radiology information, etc. LCD screen 56 may include a graphical user device that enables the surgeon to select different feedback profiles, adjust sensor behavior, modify supplemental information, etc.

LCD screen 56 may also include a control slider device 58, which can be designed to allow the operator to make adjustments to the image or contour information provided on LCD screen 56. In other embodiments, control slider device 58 may instead be configured using other types of control devices, such as buttons, switches, etc., for controlling image information.

Figure 4:
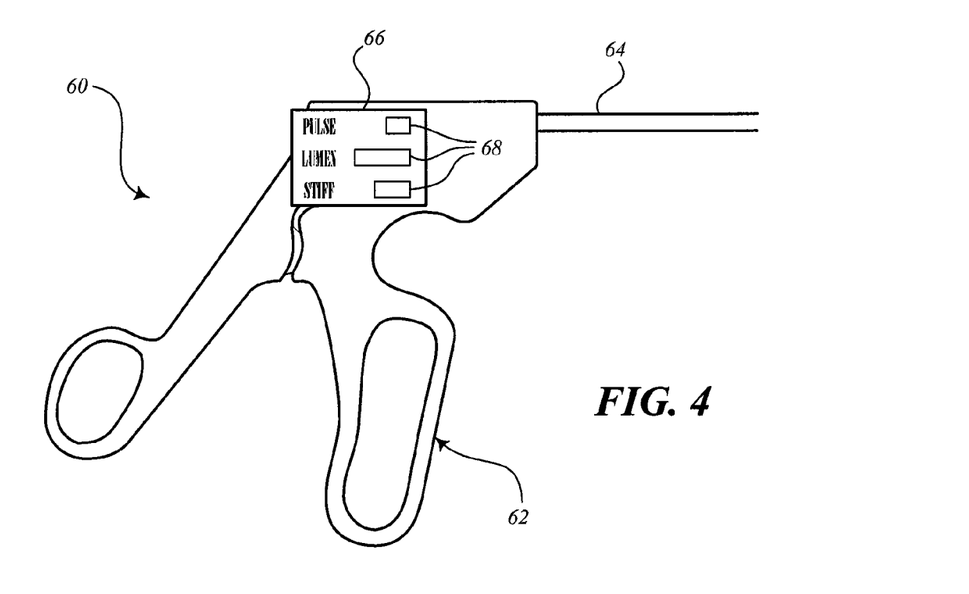
FIG. 4 is a diagram illustrating a side view of a surgical tool having a device for providing visual and haptic output to an operator, according to one embodiment.

FIG. 4 is a diagram showing an embodiment of a surgical tool 60 from a side view. This embodiment and other embodiments illustrated herein are particularly implemented for right-handed surgeons. It should be understood, however, that a reversed or mirror-image implementation can be obtained for use by left-handed surgeons. In this diagram, only a handle portion 62 and part of a shaft 64 are shown of surgical tool 60, which may include other features, such as a sensing device at a distal portion thereof. In this embodiment, handle portion 62 supports a display device 66. Display device 66 may be configured to provide any type of indication of properties of the object under test. For example, various properties can be sensed by one or more distal sensors or can result from different algorithmic applications during processing of sensed signals.

In the embodiment of FIG. 4, display device 66 provides information about pulse, lumen, and stiffness of the object. For example, pulse indication refers to a pulse of a blood vessel of a patient when this vital statistic is measured. The lumen indication refers to the presence or absence of a hollow tissue structure (lumen) such as a ureter, bile duct, or the like. The stiffness indication refers to the stiffness of an organ or tissues in contact with a sensor at the distal end of surgical tool 60.

Display device 66 can provide indication of particular parameters by the use of bar indicators 68, where the length of the bar of each respective bar indicator 68 represents an intensity or level of the respective parameter. Bar indicators 68 of display device 66 can be configured to provide output information both visually and haptically. For example, since display device 66 is positioned on the side of handle portion 62, the operator may be able to look at the side of surgical tool 60 during use to see display device 66. In addition, the index finger of the operator can be placed on the surface of display device 66 to haptically sense display device 66. In this respect, bar indicator 68 includes any suitable haptic output device, shape changing device, etc., to communicate the particular information to the operator using the sense of touch. Therefore, the operator can feel the length of bar indicators 68 to receive the needed feedback signals as needed, even without visually observing display device 66.

Figure 5:
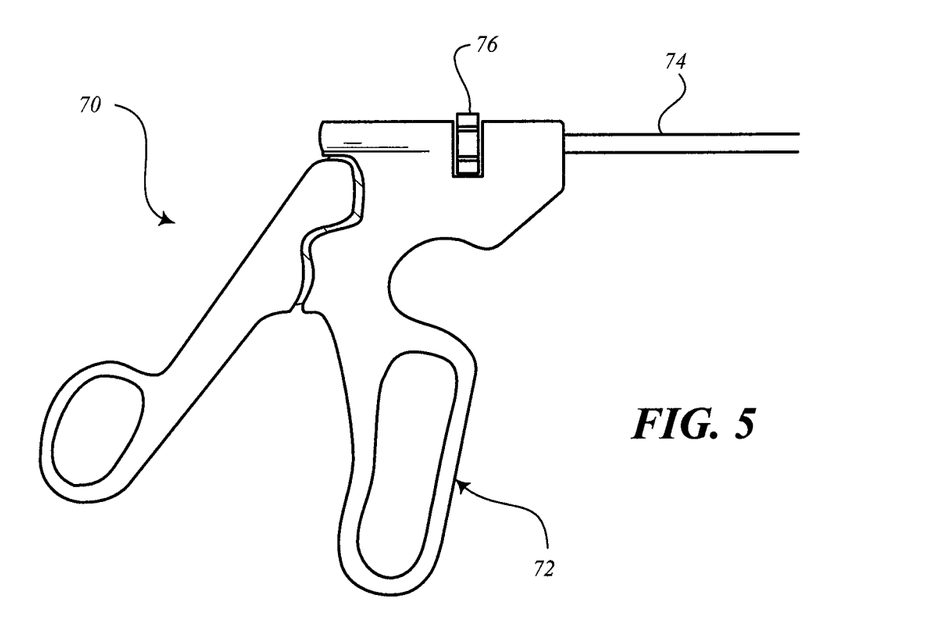
FIG. 5 is a diagram illustrating a side view of a surgical tool having a rotary device, according to one embodiment.

FIG. 5 is a diagram showing an embodiment of a surgical tool 70 from a side view. In this diagram, only a handle portion 72 and part of a shaft 74 are shown of surgical tool 70, which may include other features, such as a sensing device at a distal portion thereof. Handle portion 72, according to this embodiment, includes, among other things, a rotary device 76, which can be used as a "roll" control device. Rotary device 76 is connected to shaft 74 and, when rotated by operator, is configured to rotate shaft 74 about its axis. Likewise, a sensor connected to a distal portion of surgical tool 70 rotates in response to rotation of rotary device 76. In this way, the operator can control the positioning of the sensor to pick up various signals from different sensed regions of the patient.

In this embodiment, vibrotactile, haptic, kinesthetic, and/or resistive feedback can be incorporated into rotary device 76 to indicate directly certain information through rotary device 76 itself. According to one example, a vibrotactile actuator may vibrate rotary device 76 at an amplitude based on the stiffness of the region of the patient being sensed. In another example, a sensor can be mounted on a perpendicular face of the shaft axis or distal end and oriented toward the side. Using the roll control, the sensor sweeps around the axis to observe the surrounding tissue and identify vasculature, tumor masses, etc., using visual sensor, stiffness sensor, or other suitable sensors.

Figure 6:
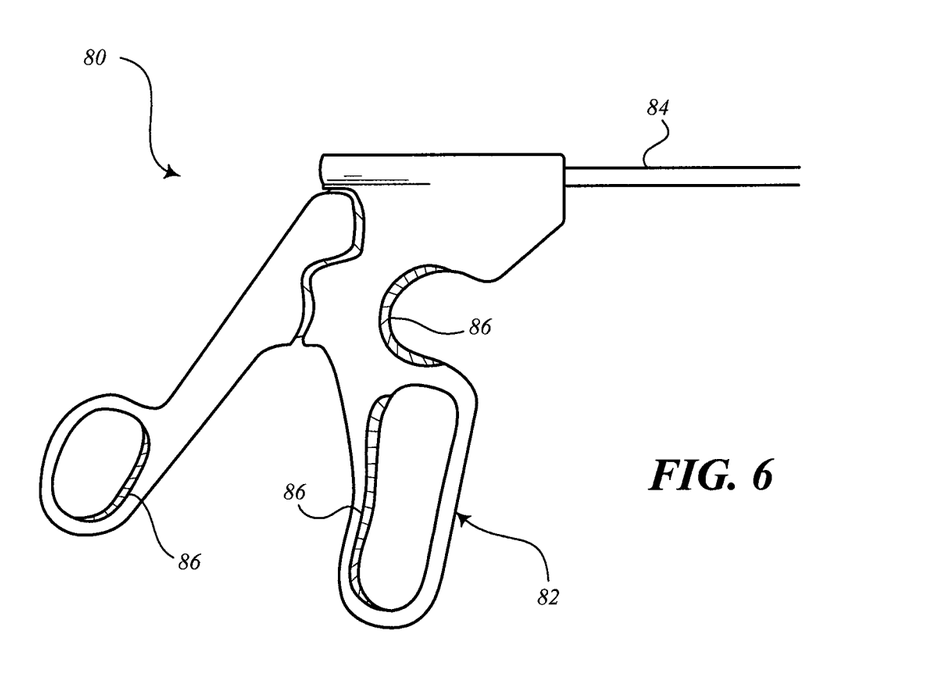
FIG. 6 is a diagram illustrating a side view of a surgical tool having haptic actuating devices formed in the handle thereof, according to one embodiment.

FIG. 6 is a diagram showing an embodiment of a surgical tool 80 from a side view. In this diagram, only a handle portion 82 and part of a shaft 84 are shown of surgical tool 80, which may include other features, such as a sensing device at a distal portion thereof. In this embodiment, surgical tool 80 includes haptic actuating devices 86 incorporated in the handle portion 82 for providing haptic effects to the fingers and thumb of a hand of the surgeon. Haptic actuating devices 86 may be configured to provide feedback signals based on signals sensed at the distal portion of surgical tool 80. Haptic actuating devices 86 may include ERM actuators, LRAs, shape memory alloys, electromagnetic motors, electro-active polymers that deform in response to signals, mechanism for changing stiffness, vibrotactile actuators, inertial actuators, piezoelectric actuators, etc. In one example, a grasping characteristic can be used to convey contact force, pressure, etc., on haptic actuating devices 86.

Haptic actuating devices 86 may be able to sense pressure applied by the user. In response to the pressure, haptic actuating devices 86 may be configured to provide an alert that the user may be squeezing handle portion 82 too hard or too soft. Haptic actuating devices 86 may also be configured to communicate sensed information to the user.

Figure 7:
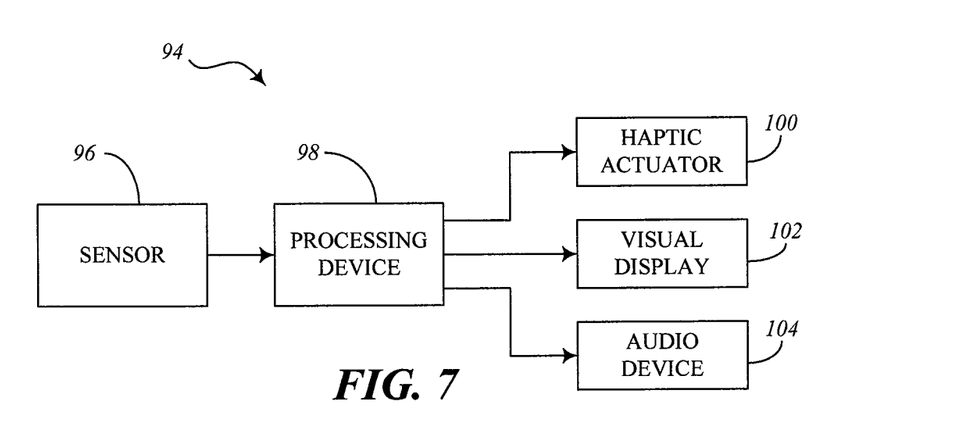
FIG. 7 is a block diagram of a system for communicating sensed properties to an operator, according to one embodiment.

FIG. 7 is a block diagram illustrating an embodiment of a system 94 for controlling how sensed signals are provided to an operator. In this embodiment, system 94 includes one or more sensors 96, a processing device 98, one or more haptic actuators 100, one or more visual displays 102, and one or more audio devices 104. Sensor 96 may be positioned on a portion of a tool, e.g., a distal end of a tool used for probing an object. Sensor 96 is configured to include any type of sensing mechanisms to sense any suitable characteristic of the object.

The sensed information from each of the one or more sensors 96 is communicated to processing device 98, which is configured to process the information according to specific algorithms and operator selections. Processing device 98, for example, may correspond to processing device 24 shown in FIG. 1. Depending on the type of sensing mechanisms of sensors 96 and the type of properties being measured, the algorithms of processing device 98 can determine various characteristics of the object. Processing device 98 also takes into account operator input regarding enabling or disabling one or more output mechanisms, adjusting of levels of the one or more output mechanisms, etc. Processing device 98 may then communicate the processed information to one or more of haptic actuator 100, visual display 102, and audio device 104 according to which ones of these output mechanisms are enabled and how they are controlled to provide their respective outputs. Haptic actuator 100, visual display 102, and audio device 104 represent the output mechanisms that are designed to present the sensor information to the operator.

Processing device 98 may be a general-purpose or specific-purpose processor or microcontroller for processing the signals detected by sensor 96. In some embodiments, processing device 98 may include a plurality of processors for performing different functions with respect to system 94. In some embodiments, processing device 98 may be associated with a memory device (not shown) for storing data and/or instructions. In this regard, the memory may include one or more internally fixed storage units, removable storage units, and/or remotely accessible storage units, and the various storage units may include any combination of volatile memory and non-volatile memory. Logical instructions, commands, and/or code can be implemented in software, firmware, or both, and stored in memory. In this respect, the logic code may be implemented as one or more computer programs that can be executed by processing device 34.

In other embodiments, logical instructions, commands, and/or code can be implemented in hardware and incorporated in processing device 98 using discrete logic circuitry, an application specific integrated circuit ("ASIC"), a programmable gate array ("PGA"), a field programmable gate array ("FPGA"), etc., or any combination thereof. In yet other embodiments, logical instructions, commands, and/or code can be implemented in both hardware in processing device 98 and software/firmware stored in the memory.

Each output device represented by haptic actuator 100, visual display 102, and audio device 104 may include one or more of the respective output devices in any suitable form for providing haptic, visual, or audio outputs to the operator. Also, some output devices may be capable of providing multiple modes of communication in any combination. The output mechanisms may include any number of feedback mechanisms in any number of modes for providing any type of visual, audible, and/or tactile output to the operator. In the embodiments regarding surgical tools, the output mechanisms may be set up to provide feedback to the surgeon according to the surgeon's preferences. With feedback tailored to the surgeon's desires, the tool can provide feedback to supplement the operator experience for better operation and performance.

Figure 8:
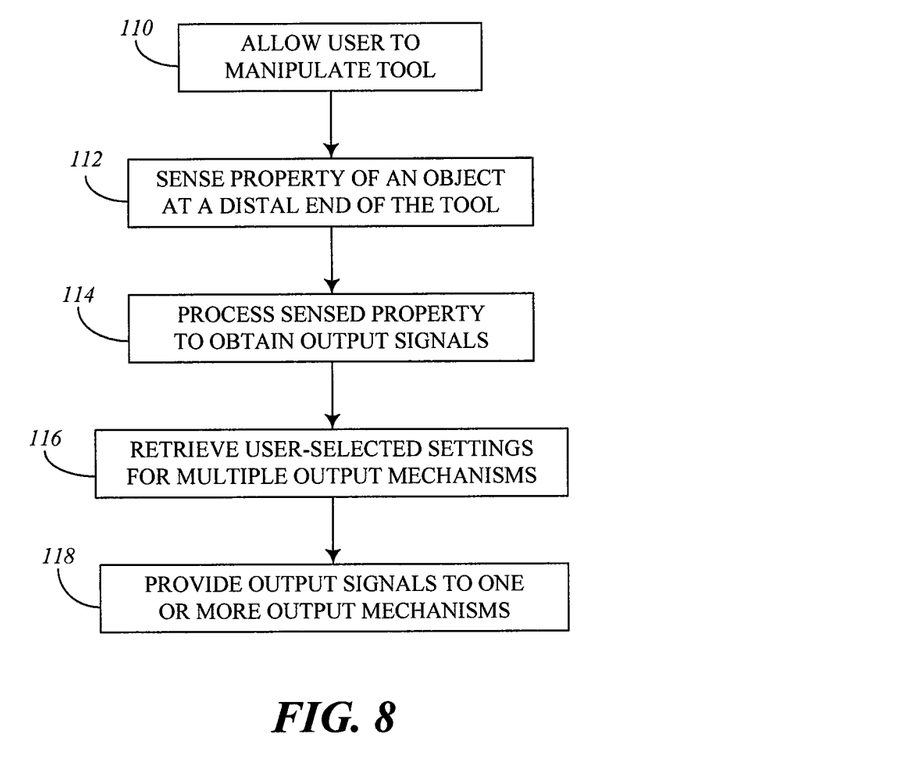
FIG. 8 is a flow diagram illustrating a method for controlling signals sensed by a sensor mounted on a tool, according to one embodiment.

FIG. 8 is a flow diagram of an embodiment of a method of operation of a tool having multiple modes of feedback. As indicated in block 110, an operator is allowed to manipulate a tool according to a normal use of the tool. For example, the operator may manipulate a handle, buttons, or other feature on the tool to control a functional portion of the tool. The controlled portion may be a portion that is positioned on an opposite end of the tool from the handle. The controlled portion can be probed around to contact an object being tested or to be placed in proximity to the object being tested, depending on the particular type of parameter being measured.

As indicated in block 112, one or more properties of an object are sensed at a distal end of the tool. Particularly, the property or properties may be sensed by one or more sensing devices. The sensors may be positioned on or near the controlled portion of the tool. According to block 114, the sensed properties are processed to obtain output signals. Based on the properties sensed and the types of output mechanisms incorporated in tool, output signals can be obtained for each particular output mechanism.

As indicated in block 116, operator selected settings are retrieved. In particular, the settings are selected to define how the output mechanisms are to be used in response to sensed signal. For example, the operator selected settings may include whether each respective output mechanism is enable or disabled, or turned on or off. Also, the settings may include level adjustment for factors associated with the different types of modes of communication, such as a haptic mode, visual mode, auditory mode, etc.

As indicated in block 118, the output signals are provided to the one or more output mechanisms. Thus, the sensed signals are communicated to the operator in one or more different output modes, depending on the modes selected by the operator. The outputs may be haptic outputs, vibrotactile effect outputs, visual outputs, auditory outputs, or any combination of these or other outputs.

It should be understood that the routines, steps, processes, or operations described herein may represent any module or code sequence that can be implemented in software or firmware. In this regard, these modules and code sequences can include commands or instructions for executing the specific logical routines, steps, processes, or operations within physical components. It should further be understood that two or more of the routines, steps, processes, and/or operations described herein may be executed substantially simultaneously or in a different order than explicitly described, as would be understood by one of ordinary skill in the art.

The embodiments described herein represent a number of possible implementations and examples and are not intended necessarily to limit the present disclosure to any specific embodiments. Instead, various modifications can be made to these embodiments as would be understood by one of ordinary skill in the art. Any such modifications are intended to be included within the spirit and scope of the present disclosure and protected by the following claims.

What is claimed is:

1. A surgical tool for performing a minimally invasive surgical procedure comprising:
   a handle portion and a distal portion;
   a sensor mounted on the distal portion, the sensor configured to generate sensor signals representing one or more characteristics of an object located near or adjacent to the distal portion of the surgical tool;
   a processing device configured to process the sensor signals to generate one or more output signals; and
   an output system for providing multiple outputs from the one or more output signals, the output system including a display device mounted on the handle portion, wherein the processing device is further configured to provide the one or more output signals to the display device and wherein the display device includes bar indicators that provide a visual output and a haptic output based on the output signals to provide feedback relating to the one or more characteristics of the object, wherein to provide the haptic output the bar indictors have surfaces that raise to correspond to a shape of the visual output.

2. The tool of claim 1, wherein the haptic output includes changes in a length of one or more of the bar indicators that can be felt by a user.

3. The tool of claim 1, wherein the bar indicators provide information about a pulse of a blood vessel, presence or absence of a lumen and stiffness of the object.

4. A surgical tool for performing a minimally invasive surgical procedure comprising:
   a handle portion and a distal portion;
   a sensor mounted on the distal portion, the sensor configured to generate sensor signals representing one or more characteristics of an object located near or adjacent to the distal portion of the surgical tool;
   a processing device configured to process the sensor signals to generate one or more output signals; and
   an output system for providing multiple outputs from the one or more output signals, the output system including a display device mounted on the handle portion, wherein the processing device is further configured to provide the one or more output signals to the display device, wherein the display device is a liquid crystal display screen that is configured to provide a haptic output and a visual output based on the output signals to provide feedback relating to the one or more characteristics of the object, wherein the liquid crystal display screen has a surface that changes shape or size based on the output signals such that the surface raises so that it takes a shape or size to correspond to a shape or size of the visual output.

5. The tool of claim 4, wherein a topography of the surface of the liquid crystal display screen adjusts to provide an indication of the topography of the object being sensed.

6. The tool of claim 1, wherein the surgical tool is a laparoscopic tool.

7. The tool of claim 4, wherein the surgical tool is a laparoscopic tool.

* * * * *